US006936742B2

United States Patent
Smith, Jr.

(10) Patent No.: US 6,936,742 B2
(45) Date of Patent: Aug. 30, 2005

(54) PRODUCTION OF DIISOBUTENE FROM TERTIARY BUTYL ALCOHOL

(75) Inventor: Lawrence A. Smith, Jr., Houston, TX (US)

(73) Assignee: Catalytic Distillation Technologies, Pasadena, TX (US)

(*) Notice: Subject to any disclaimer, the term of this patent is extended or adjusted under 35 U.S.C. 154(b) by 266 days.

(21) Appl. No.: 10/382,899

(22) Filed: Mar. 6, 2003

(65) Prior Publication Data

US 2004/0006252 A1 Jan. 8, 2004

Related U.S. Application Data

(60) Provisional application No. 60/364,885, filed on Mar. 15, 2002.

(51) Int. Cl.[7] .............................................. C07C 1/207
(52) U.S. Cl. ................... 585/327; 585/639; 203/DIG. 6
(58) Field of Search ............................... 585/327, 639; 203/DIG. 6

(56) References Cited

U.S. PATENT DOCUMENTS

| 4,242,530 A | 12/1980 | Smith, Jr. ................... 585/510 |
| 4,375,576 A | 3/1983 | Smith, Jr. ................... 585/510 |
| 4,447,668 A | 5/1984 | Smith, Jr. et al. ........... 585/639 |
| 5,231,234 A | 7/1993 | Arganbright et al. ....... 568/697 |

*Primary Examiner*—Thuan D Dang
(74) *Attorney, Agent, or Firm*—Kenneth H. Johnson

(57) ABSTRACT

A process for the production of diisobutene is disclosed wherein tertiary butyl alcohol is dehydrated to isobutene in a distillation column reactor containing an acid cation exchange resin catalyst in the form of catalytic distillation structure. The isobutene reacts with itself in the presence of the catalyst to form primarily diisobutene which is removed as bottoms from the distillation column reactor with the bulk of the water. Unreacted isobutene along with an azeotrope of water is removed as overheads with the water being separated and removed from the unreacted isobutene. A portion or all of the unreacted isobutene may be returned to the distillation column reactor as reflux.

7 Claims, 1 Drawing Sheet

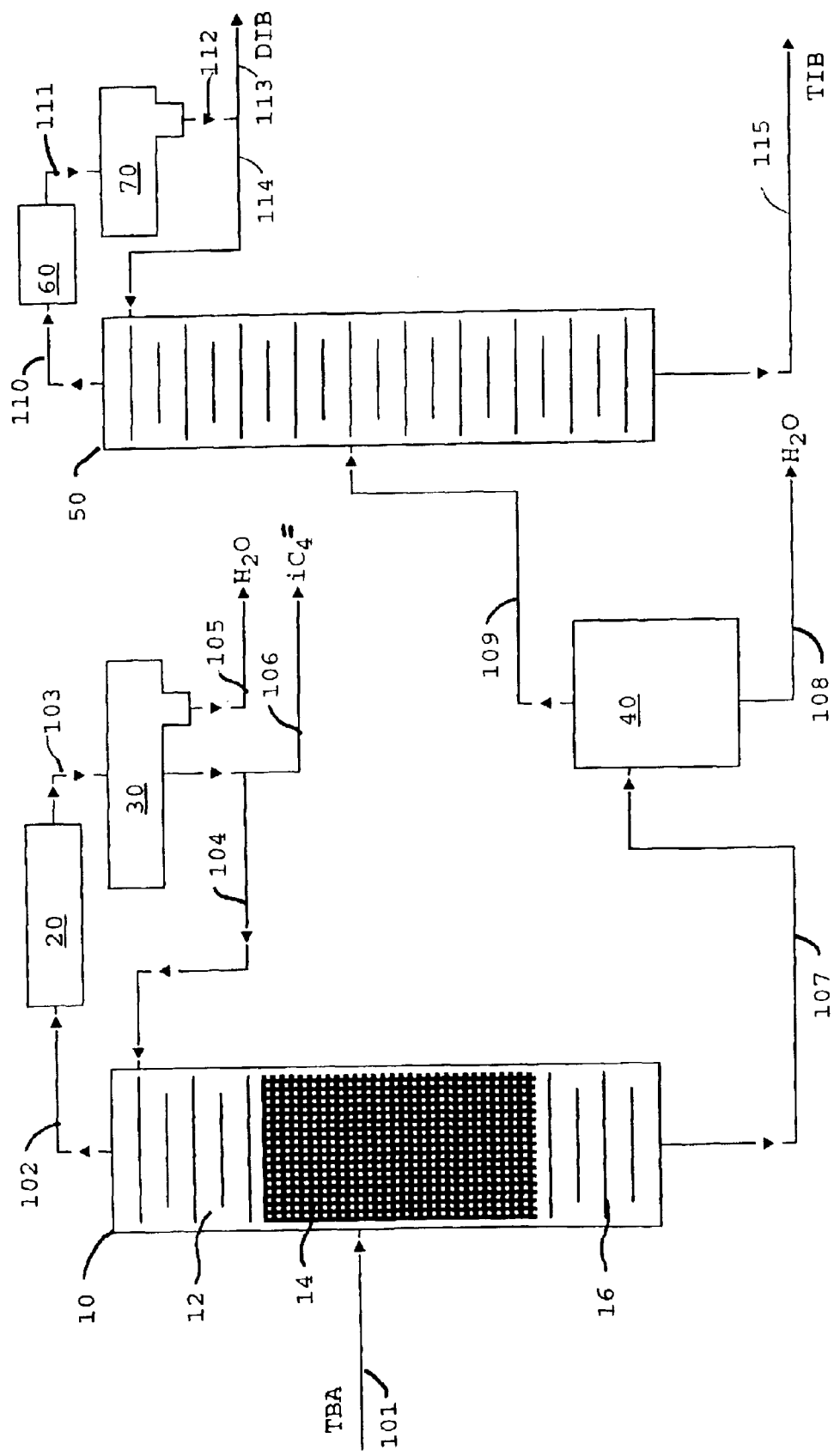

PRODUCTION OF DIISOBUTENE FROM TERTIARY BUTYL ALCOHOL

This application claims benefit of provisional application No. 60/364,885, filed Mar. 15, 2002.

BACKGROUND OF THE INVENTION

1. Field of the Invention

The present invention relates to an integrated process for the production of isobutene by the concurrent dehydration of tertiary butyl alcohol (TBA) and the oligomerization of the butenes to form diisobutene (DIB). More particularly the invention relates to a process wherein the dehydration and oligomerization are carried out in a distillation column reactor wherein substantially all of the TBA is dehydrated and unreacted isobutene is removed by fractional distillation as an overheads.

2. Related Art

Isobutene and diisobutene are of significant value having diverse applications, for example, isobutene is one of the comonomers for butyl rubber and diisobutene is an intermediate in the preparation of detergents. The isobutene oligomers are useful as polymer gasoline. In particular diisobutene may be hydrogenated to produce essentially pure 2,2,4 tri-methyl pentane or isooctane.

In the past other processes have used various catalysts for converting the isobutene to diisobutene. For example, a process using a molecular sieve and elevated temperature is disclosed in U.S. Pat. No. 3,531,539. In U.S. Pat. No. 3,518,323 a supported nickel oxide catalyst is used. In U.S. Pat. No. 3,832,418 a Group VI or VIII metal deposited on acidic, amorphous silica-alumina is used in the same manner. Finally, U.S. Pat. No. 4,215,100 discloses the use of an acid cation exchange resin in a heterogenous combination reaction/distillation system for the selective dimerization of isobutene in the presence of normal butenes. Although some codimer between n-butenes and isobutene are formed, the reaction is highly preferential for the reaction of isobutene with itself and provides a means to separate isobutene from a $C_4$ stream with little loss of other butenes. Recently U.S. Pat. No. 6,274,783 disclosed a process for the concurrent production and hydrogenation of diisobutene in a single distillation column reactor containing both a dimerization catalyst and a hydrogenation catalyst by the dimerization of isobutene to diisobutene.

U.S. Pat. No. 5,231,234 discloses the two stage production of methyl tertiary butyl ether utilizing the dehydration of tertiary butyl alcohol in a first stage distillation column reactor to produce isobutene. The amount of water in the reactor is controlled to keep the catalyst wetted and thus prevent the oligomerization of the isobutene.

SUMMARY OF THE INVENTION

Briefly, the present invention is a process for the production of diisobutene comprising the steps of:

(a) feeding tertiary butyl alcohol to a distillation column reactor into a feed zone;

(b) concurrently in said distillation column reactor (i) contacting said tertiary butyl alcohol with an acid ion exchange resin catalyst as a component in distillation structure in a distillation reaction zone under conditions of temperature and pressure to dissociate said tertiary butyl alcohol to isobutene and water and to react a portion of the isobutene with itself to form diisobutene and (ii) separating said diisobutene from unreacted isobutene and said water by fractional distillation;

(c) withdrawing said unreacted isobutene and water from said distillation column reactor as overheads; and (d) withdrawing said diisobutene and water from said distillation column reactor as bottoms;

(e) separating the water from said diisobutene; and as required (f) separating said diisobutene from heavier oligomers such as tri-isobutene by fractional distillation.

The acid ion exchange resin catalyst is in such a form as to act as both the catalyst for the reaction and distillation structure for the fractional distillation. Suitable catalytic distillation structures are the catalyst containing cloth belts described and disclosed in U.S. Pat. Nos. 4,215,011; 4,302,356 and 4,443,559 which are incorporated by reference herein.

One preferred and commercial catalytic distillation structure described in several of the noted patents comprises a cloth belt with a plurality of pockets spaced along the belt and containing particulate catalyst material, said cloth belt being wound in a helix about a spacing material such as stainless steel knitted mesh. These units are then disposed in the distillation column reactor. In addition, U.S. Pat. No. 4,250,052 discloses a variety of catalytic distillation structures for this use and is incorporated herein. The newest commercial catalytic distillation structure for use in reaction distillation including the present reaction is disclosed in U.S. Pat. No. 5,730,843.

The operation of catalytic distillation lies in an understanding of the principles associated with distillation. Because the reaction is occurring concurrently with distillation, the initial reaction product is removed from the reaction zone as quickly as it is formed which minimizes further reaction. The heat of the reaction, if any, simply creates more boil up, but no increase in temperature.

BRIEF DESCRIPTION OF THE DRAWING

The FIGURE is a flow diagram in schematic form of one embodiment of the present invention.

DESCRIPTION OF THE PREFERRED EMBODIMENT

1. Catalyst and Distillation Structure

Suitable acid cation exchange resins include those which contain sulfonic acid groups, and which may be obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinyl phenylether and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric and chlorosulfonic acid, or by copolymerizing aromatic compounds which contain sulfonic acid groups (see e.g., U.S. Pat. No. 2,366,007). Further sulfonic acid groups may be introduced into the polymers which already contain sulfonic acid groups; for example, by treatment with fuming sulfuric acid, i.e., sulfuric acid which contains sulfur trioxide. The treatment with fuming sulfuric acid is preferably carried out at 0 to 150° C. and the sulfuric acid should contain sufficient sulfur trioxide so that it still contains 10 to 50% free sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Pat. No. Specification 908,240). The ion exchange resin is generally used in a granular size of about 0.25 to 1 mm, although particles from 0.15 mm up to about 2 mm may be employed. The finer catalysts provide high surface area, but also result in high pressure drops through the reactor. The macroreticular form of these catalysts have much larger surface area exposed and limited swelling which all of these resins undergo in a non-aqueous hydrocarbon medium compared to the gelular catalysts.

The container employed to hold the catalyst particles may have any configuration, such as the pockets disclosed in the patents above or the container may be a single cylinder, sphere, doughnut, cube, tube or the like.

Each container containing a solid catalytic material comprises a catalyst component. Each catalyst component is intimately associated with a spacing component which is comprised of at least 70 volume % open space up to about 95 volume % open space. This component may be rigid or resilient or a combination thereof. The combination of catalyst component and spacing component form the catalytic distillation structure. The total volume of open space for the catalytic distillation structure should be at least 10 volume % and preferably at least 20 volume % up to about 65 volume %. Thus, desirably the spacing component or material should comprise about 30 volume % of the catalytic distillation structure, preferably about 30 volume % to 70 volume %. Resilient materials are preferred. One suitable such material is open mesh knitted stainless wire, known generally as demister wire or an expanded aluminum. Other resilient components may be similar open mesh knitted polymeric filaments of nylon, teflon and the like. Other materials such as highly open structures foamed material, e.g., reticulated polyurethane foam (rigid or resilient) may be formed in place or applied around the catalyst component.

In the case of larger catalyst components such as from about ¼ inch to ½ pellets, spheres, pills and the like, each such larger component may be individually intimately associated with or surrounded by the spacing component as described above.

It is not essential that the spacing component entirely cover the catalyst component. It is only necessary that the spacing component intimately associated with the catalyst component will act to space the various catalyst components away from one another as described above. Thus, the spacing component provides in effect a matrix of substantially open space in which the catalyst components are randomly but substantially evenly distributed.

A preferred catalytic distillation structure for use herein comprises placing the cation exchange resin particles into a plurality of pockets in a cloth belt, which is supported in the distillation column reactor by open mesh knitted stainless steel wire by twisting the two together in a helical form. This allows the requisite flows and prevents loss of catalyst. The cloth may be any material which is inert in the reaction. Cotton or linen is useful, but fiber glass cloth or "Teflon" cloth is preferred.

In a preferred mode the catalyst packing consists of bags in the form of a fiber glass cloth belt approximately six inches wide with narrow pockets approximately ¾ inch wide sewn across the belt. These pockets are filled with the catalyst particles to form approximately cylindrical containers, and the open ends are then sewn closed to confine the particles. This belt is then twisted into a helical form to fit inside the column. Twisted in with the belt is also a strip of an open mesh knitted stainless steel wire, which serves to separate the catalyst filled cloth pockets and provide a passage for vapor flow.

The wire mesh provides the support for the catalyst belt and provides some degree of vapor passage through the catalyst particles, which otherwise form a very compact bed which has a high pressure drop. Thus, the down flowing liquid is in intimate contact with the rising vapors and the catalyst in the column.

Catalyst packing may be made up of alternating layers of catalyst filled cloth belts similar to the ones described above, and a spacing material which could be of any convenient, suitable substance, such as a corrugated wire screen or wire cloth or a knitted wire mesh. The layers would be arranged vertically or horizontally. For simplicity of fabrication and for better distribution of vapor flow passages, a vertical orientation is preferred. The height of a section of this packing could be of any convenient dimension, from a few inches to several feet. For ease of assembly and installation, the packing would be made into sections of the desired shape and size, each section fastened together with circumferential bands of tie wires depending on its size and shape. A complete assembly in a column would consist of several sections, arranged in layers, with possibly the orientation of the catalyst-filled belts turned at right angles in successive layers to improve liquid and vapor flow distribution.

2. Process Description

The reaction system can be described as heterogeneous since the catalyst remains as a distinct entity.

Bulk type liquid phase reactions have as one problem the control of the temperature. The distillation avoids the problem entirely. Because the reaction is occurring concurrently with distillation, the initial reaction products are removed from the reaction zone nearly as quickly as they are formed. The removal of diisobutene from the dehydration is important because the newly formed diisobutene has a tendency to react with itself or other isobutene in the presence of acid catalyst to form higher oligomer.

The tendency of isobutene to react with itself in the dehydration column is promoted by removal of the water in that column to keep the catalyst dry and also by operating the dissociation at higher temperatures.

Also in the distillation column reactor because the mixture is boiling, the temperature of the reaction is controlled by the boiling point of the mixture in the reactor at the system pressure. The heat of the reaction, which is exothermic, simply consumes more boil up with no change in temperature. That is, if the heat is added in excess, there is no harm done since the excess will only result in more boil up. Third, the reaction has an increased driving force because the reaction products have been removed and cannot contribute to the reverse reaction (Le Chatelier's Principle). Thus, a great deal of control over the rate of reaction and distribution of products can be achieved by regulating the system pressure. Also, adjusting the throughput (residence time=liquid hourly space velocity$^{-1}$) gives further control of product distribution.

In the distillation column reactor higher temperatures favor oligomerization. It has been found however that to promote the oligomerization, the catalyst is preferably maintained "dry", that is, the conditions of operation are such as to remove the water produced in the dehydration in the catalyst zone as soon as possible either as overheads in an azeotrope or as bottoms.

A reflux is preferably included in the distillation column reactor. The reflux ratio could vary over the rate of 0.5 to 25:1. In practice, the higher ratio may be used to compensate for a short catalyst bed such as required for experimental work. In commercial size units the catalyst bed would be provided so that lower reflux and hence higher unit productivity could be obtained, e.g., 0.5 to 2:1.

Referring now to the FIGURE a typical flow scheme is shown in simplified schematic form. Tertiary butyl alcohol (TBA) is fed via flow line 101 into distillation column reactor 10 into the catalyst 14 prepared as described as distillation structures. In the catalyst bed 14 the TBA is dehydrated to isobutene with unreacted isobutene. An azeotrope of water/isobutene is taken as overheads via flow line 102. Rectification section 12 above the catalyst bed prevents any TBA from being taken as overheads. The overheads are cooled in condenser 20 and collected in receiver 30 where the water is separated and removed via flow line 105. The unreacted isobutene is withdrawn and a portion or all returned as reflux via flow line 104. If desired a slip stream of isobutene may be removed via flow line 106.

The isobutene reacts with itself in the catalyst bed to form oligomers of butene, preferably diisobutene, but some higher oligomers such as tri-isobutene may also result. The higher boiling oligomers and water are removed as bottoms from the distillation column reactor via flow line 107 and fed to a phase separator where the water is removed via flow line 108. The hydrocarbon phase containing the oligomers is then fed via flow line 109 to a distillation column 50 where the diisobutene is separated as overheads in flow line 110 from the higher oligomers, here tri-isobutene, as bottoms in flow line 115. The diisobutene is condensed in condenser 60 and collected in receiver 70. The liquid product is removed from the receiver via flow line 112 with a portion being returned to the distillation column 50 as reflux via flow line 114. The final product diisobutene is removed via flow line 113.

The invention claimed is:

1. A process for the production of diisobutene comprising the steps of:
   (a) feeding tertiary butyl alcohol to a distillation column reactor into a feed zone;
   (b) concurrently in said distillation column reactor
      (i) contacting said tertiary butyl alcohol with an acid ion exchange resin catalyst as a component in distillation structure in a distillation reaction zone under conditions of temperature and pressure to dissociate said tertiary butyl alcohol to isobutene and water to react a portion of the isobutene with itself to form diisobutene and to remove water and maintain the acid ion exchange resin catalyst in a dry condition and
      (ii) separating said diisobutene from unreacted isobutene and said water by fractional distillation;
   (c) withdrawing said unreacted isobutene and water from said distillation column reactor as overheads; and
   (d) withdrawing said diisobutene and water from said distillation column reactor as bottoms; and
   (e) separating the water from said diisobutene.

2. The process according to claim 1 comprising:
   (f) separating said diisobutene from heavier oligomers by fractional distillation.

3. The process according to claim 1 wherein said heavier oligomers comprise tri-isobutene.

4. The process according to claim 1 wherein said overheads are condensed and further comprising the steps of separating the water from said unreacted isobutene.

5. The process according to claim 4 wherein a portion of the separated isobutene is returned to said distillation column reactor as reflux.

6. The process according to claim 4 wherein all of the separated isobutene is returned to said distillation column reactor as reflux.

7. A process for the production of diisobutene comprising the steps of:
   (a) feeding tertiary butyl alcohol to a distillation column reactor into a feed zone;
   (b) concurrently in said distillation column reactor
      (i) contacting said tertiary butyl alcohol with an acid ion exchange resin catalyst as a component in a distillation structure in a distillation reaction zone under conditions of temperature and pressure to dissociate said tertiary butyl alcohol to isobutene and water and to remove water and maintain the acid ion exchange resin catalyst in a dry condition,
      (ii) reacting a portion of the isobutene with itself to form diisobutene and tri-isobutene in said distillation reaction zone,
      (iii) separating said diisobutene and tri-isobutene from unreacted isobutene and said water by fractional distillation;
   (c) withdrawing said unreacted isobutene and water from said distillation column reactor as overheads;
   (d) condensing said overheads;
   (e) separating the water from the unreacted isobutene;
   (f) returning a portion of the unreacted isobutene to said distillation column as reflux;
   (g) withdrawing said diisobutene, tri-isobutene and water from said distillation column reactor as bottoms;
   (h) separating the water from said diisobutene and said tri-isobutene; and
   (i) separating said diisobutene from said tri-isobutene by fractional distillation.

* * * * *